United States Patent
Friese et al.

[11] Patent Number: 5,885,429
[45] Date of Patent: Mar. 23, 1999

[54] ELECTROCHEMICAL MEASURING SENSOR AND METHOD FOR PRODUCING AN ELECTROCHEMICAL MEASURING SENSOR

[75] Inventors: Karl-Hermann Friese, Leonberg; Werner Gruenwald, Gerlingen; Kurt Schmid, Ditzingen; Claudio De La Prieta, Stuttgart; Gerhard Schneider, Vaihingen; Hans-Joerg Renz, Leinfelden-Echterdingen; Harald Neumann, Vaihingen; Uwe Glanz, Asperg; Stefan Kuschel, Stuttgart; Ralf Haug, Leonberg; Manfred Moser, Reutlingen-Sickenhausen; Kurt Bayha, Oberriexingen; Annette Seibold, Rutesheim; Carmen Schmiedel, Benningen; Reiner Schuetz, Ditzingen, all of Germany

[73] Assignee: Robert Bosch GmbH, Stuttgart, Germany

[21] Appl. No.: 860,661

[22] PCT Filed: Sep. 17, 1996

[86] PCT No.: PCT/DE96/01753

§ 371 Date: Aug. 8, 1997

§ 102(e) Date: Aug. 8, 1997

[87] PCT Pub. No.: WO97/17608

PCT Pub. Date: May 15, 1997

[30] Foreign Application Priority Data

Nov. 8, 1995 [DE] Germany .......... 195 41 619.8

[51] Int. Cl.$^6$ ..................... G01N 27/26
[52] U.S. Cl. ................ 204/427; 204/425
[58] Field of Search ................ 204/427, 425, 204/426

[56] References Cited

U.S. PATENT DOCUMENTS

| | | | |
|---|---|---|---|
| 4,294,679 | 10/1981 | Maurer et al. | 204/195 S |
| 4,810,529 | 3/1989 | Mantese et al. | 204/427 |
| 4,851,105 | 7/1989 | Ishiguro et al. | 204/429 |
| 5,215,643 | 6/1993 | Kusanagi et al. | 204/412 |

FOREIGN PATENT DOCUMENTS

| | | |
|---|---|---|
| OS2928496 | 1/1981 | Germany . |
| A1591898 | 7/1981 | Germany . |
| OS3804683 | 8/1988 | Germany . |

*Primary Examiner*—Bruce F. Bell
*Attorney, Agent, or Firm*—Venable; George H. Spencer; Norman N. Kunitz

[57] ABSTRACT

An electrochemical measuring sensor having a solid electrolyte, a first electrode exposed to a gas to be measured and a second electrode exposed to a reference gas, with the electrodes preferably being arranged on opposite sides of the solid electrolyte. At least one of the electrodes (16, 20) is provided with a contouring (24) on its side (22) that is exposed to the gas to be measured or to the reference gas, with the contouring being a trench-shaped groove (26) embossed into the surface of the electrode such that the electrode is pressed into the adjacent solid electrolyte in the region of the groove. According to the method, the embossing is done while the electrode and the solid electrolyte are in the non-sintered state, and the sensor is subsequently sintered.

8 Claims, 2 Drawing Sheets

ELECTROCHEMICAL MEASURING SENSOR AND METHOD FOR PRODUCING AN ELECTROCHEMICAL MEASURING SENSOR

This application is a 371 of PCT/DE96/01753 filed Sep. 17, 1996.

The invention relates to an electrochemical measuring sensor having a solid electrolyte, a first electrode exposed to a gas to be measured and a second electrode exposed to a reference gas, with the electrodes preferably being arranged on opposite sides of the solid electrolyte, and to a method of producing an electrochemical measuring sensor having a solid electrolyte, a first electrode exposed to a gas to be measured and a second electrode exposed to a reference gas, wherein the electrodes are applied essentially layer-shaped on the solid electrolyte and the measuring sensor is subsequently sintered.

STATE OF THE TECHNOLOGY

Electrochemical measuring sensors of the generic type are known. As a rule, these have a layered structure wherein a solid electrolyte, which simultaneously acts as substrate, is provided with respectively one electrode on opposite sides. One of the electrodes is exposed to a gas to be measured and the other electrode to a reference gas, usually to atmospheric air. Corresponding to an oxygen content in the gas to be measured, a specific partial oxygen pressure appears at the electrode facing the gas to be measured. This partial oxygen pressure is at a specific ratio with respect to the partial oxygen pressure coming from the reference gas and appearing at the electrode facing the reference gas. On the basis of the resulting difference in oxygen concentration at the electrodes, a specific detector voltage occurs between the electrodes, which detector voltage can be evaluated by way of a suitable evaluation circuit and therewith supplies a signal corresponding to the oxygen concentration present at the electrode exposed to the gas to be measured. A chemical measuring sensor of this type is known, for example, from DE-OS 29 28 496, corresponding to U.S. Pat. No. 4,294,679. Here, the electrode that is exposed to the reference gas is provided with a cover. The side of the cover facing the electrode has trench-like patterns which permit a feeding of the reference gas to the electrode. Thus, the chemical measuring sensor has a design comprised of relatively many individual layers which are fixedly bonded to one another by means of a generally known sintering process. The drawback of the known design of the electrochemical measuring sensor is that the effective electrode surface, which is in direct contact with the reference gas, is relatively small compared to the actual electrode surface.

SUMMARY AND ADVANTAGES OF THE INVENTION

The electrochemical measuring sensor according to the invention offers the advantage that a relatively large effective electrode surface is available. Due to the fact that at least one of the electrodes has a contouring on its side exposed to the gas to be measured or to the reference gas, it is possible in a simple manner to make the electrode surface larger while the outer size of the electrochemical measuring sensors remains unchanged. Because of the contouring, preferably formed by trench-shaped patterns, the electrode surface of the electrode can be made larger so that a correspondingly higher electrode activity, for example, a higher pumping output, of the electrode is available.

A preferred embodiment of the invention provides that the contouring is formed by trench-shaped patterns resulting in a network pattern, which patterns are used as reference gas channels. This accomplishes in a very advantageous manner that, due to the contouring of the electrode itself that is exposed to the reference gas, the arrangement of an additional layer of the electrochemical measuring sensor, the layer being provided with the reference air channels, is no longer necessary. Thus, the design of the electrochemical measuring sensor can be simplified. Furthermore, a miniaturization of the electrochemical measuring sensor is possible because an additional layer is eliminated.

Furthermore, the method according to the invention for producing an electrochemical measuring sensor offers the advantage that, in a manner that is simple and suitable for mass production, electrochemical measuring sensors can be produced which are characterized by a simple and robust construction. Since at least one of the electrodes is contoured before sintering on its side exposed to the gas to be measured or the reference gas, it is advantageously possible, on the one hand, to utilize the contouring for an enlargement of the effective electrode surface and, on the other hand, to accomplish a greater mechanical stability of the electrode or of the measuring sensors provided with the electrode due to the contouring, so that the handling of the measuring sensors during both the production process and the mounting into a sensor element is improved.

It is particularly advantageous that the electrodes are embossed to form the contouring. Applying the embossing on the electrode prior to the sintering of the electrochemical measuring sensor is possible in a simple manner by means of a corresponding embossing stamp at a moment at which the electrode or the measuring sensor has not yet been sintered, but at which these are present as so-called green films. Therewith, these have a good deformation ability so that highly precise contouring can be accomplished by means of the embossing, which contouring remains intact after the electrochemical measuring sensor has been sintered.

Further advantageous embodiments of the invention result from the remaining features cited in the dependent claims.

DRAWINGS

The invention is explained below in greater detail by way of embodiments with reference to the associated drawings wherein.

DETAILED DESCRIPTION OF THE PREFERRED EMBODIMENTS

Figure 1:
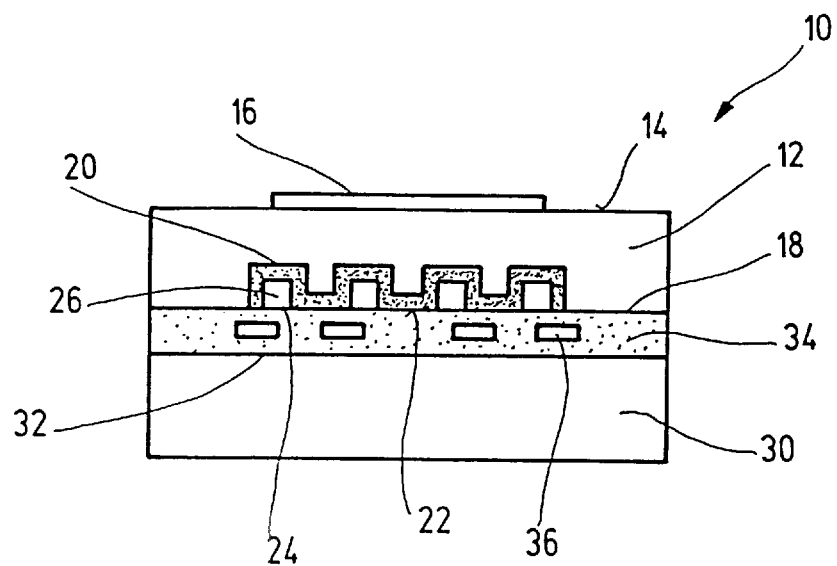
FIG. 1 is a schematic sectional representation through an electrochemical measuring sensor.

FIG. 1 shows an electrochemical measuring sensor, generally identified by 10, which sensor can be used, for example, for determining the oxygen content in gas mixtures, particularly in exhaust gases of internal combustion engines. The measuring sensor 10 is comprised of a solid electrolyte 12 on whose side 14, here shown at the top, a first electrode 16 is arranged. A second electrode 20 is arranged on the other side 18 of the solid electrolyte 12. Here, the electrode 20 is embedded in the solid electrolyte 12, so that an outer side 22 of the electrode 20 is flush with the side 18 of the solid electrolyte 12 and overall results in a planar surface.

Seen in cross section, the electrode 20 has a meander-shaped course whose design will be explained below in greater detail. The electrode 20 has a contouring 24 which is formed by trench-shaped patterns 26 which are open towards the outer side 22. As will be seen by way of FIG. 2, the trench-shaped patterns 26 form a network 28 in which trench-shaped patterns 26 that extend longitudinally to the electrode 20 cross trench-shaped patterns 26 that are arranged transversely to the electrode 20.

The side 18 of the solid electrolyte 12 is provided with a cover plate 30. The cover plate 30 closes the trench-shaped patterns 26 on the outer side 22 of the electrode 20, thus forming a branched channel system. The trench-shaped patterns 26 are thus delimited on three sides by the electrode 20 and, on their fourth side, by the cover plate 30. Optionally, a heating device 32 can be arranged in the cover plate 30, in which heating device heating conductors 36 are arranged in a layer 34.

The trench-shaped patterns 26 are open on one side of the measuring sensor 10, in particular on an end face of the measuring sensor 10, so that a reference gas can get to the electrode 20 through the network-type channel system formed by the trench-shaped patterns 26. Since the trench-shaped patterns 26 are surrounded by the electrode 20 on three sides, an effective surface of the electrode 20, which comes into direct contact with the reference gas, is relatively large. In the example that is shown, this relative surface electrode 20 is three times larger than a conventional electrode that is applied on the solid electrolyte 12 in a planar manner.

Figure 2:
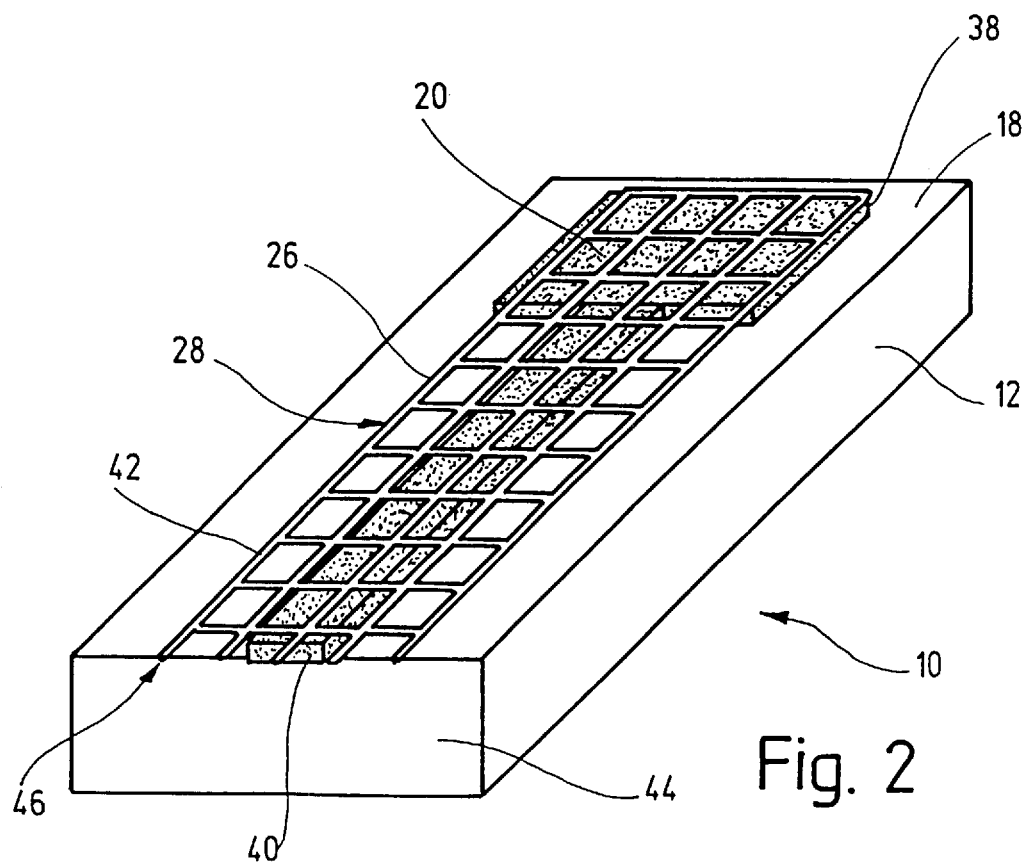
FIG. 2 is a perspective plan view onto an electrode exposed to the reference gas.

The production method for the electrochemical measuring sensor 10 will be explained in greater detail by way of FIG. 2. Parts that are identical to those in FIG. 1 are provided with identical reference numerals and will not be explained again. For reasons of clarity, the illustration of the complete measuring sensor 10 was dispensed with.

By way of the perspective plan view, it becomes clear that the solid electrolyte 12 is essentially plate-shaped. The solid electrolyte 12 is comprised, for example, of yttrium-stabilized zirconium oxide and is available in the form of a film. The electrode 20 is mounted on the side 18, here disposed on top, of the solid electrolyte 12. The electrode 20 is usually applied by means of known process steps such as, for example, imprinting. Here, the electrode 20 projects beyond the contour of the solid electrolyte 12. The solid electrolyte 12 as well as the electrode 20 and the electrode 16—not visible here—arranged on the opposite side are still present as so-called green films, that is, these have not been sintered yet.

The electrode 20 has an electrode head 38 which can be connected to a circuit arrangement, not shown, via a conductor track 40. Once the electrode 20 has been applied to the solid electrolyte 12, embossing takes place by means of an embossing stamp 42, indicated here, which has a grid pattern having the later arrangement of the network 28 that is formed by the trench-shaped patterns 26. By applying an embossing force on the embossing stamp 42, the lattice-shaped pattern of the embossing stamp 42 is imaged in the electrode 20 as well as partially in the solid electrolyte 12. The embossing force simultaneously presses the electrode 20 into the solid electrolyte 12 so that the pattern having the electrode 20 embedded in the solid electrolyte 12 is formed—as is shown in FIG. 1 in the sectional representation. Once the embossing stamp 42 is lifted, the trench-shaped patterns 26 crossing one another are left in the electrode 20.

Following the embossing process, the entire electrochemical measuring sensor 10 is sintered in a known manner so that the individual layers are tightly bonded to one another. During this process, a stabilization of the measuring sensor 10 and of the trench-shaped patterns 26 embossed in the measuring sensor 10, particularly in the electrode 20, takes place at the same time. Here, the trench-shaped patterns 26 are arranged such that, at one face side 44 of the measuring sensor 10, they have openings 46, even after they are covered with the cover plate 30 illustrated in FIG. 1, so that a reference gas can flow through the channel network which is formed by the trench-shaped patterns 26.

Overall, the electrochemical measuring sensor 10 has a very compact design which is accomplished by means of simple process steps. During this process, the individual patterns of the electrochemical measuring sensor 10 can be accomplished in the so-called panel, that is, a plurality of measuring sensors 10 can be patterned at the same time which are separated in an appropriate manner after patterning and sintering. The embossing of the electrode 20 accomplishes that the electrode 20, in particular, its electrode head 38, is supplied with the reference gas without any problems without necessitating additional complex patterns. Because of the formation of the reference air channel network by the electrode 20 itself, an optional layer 34 with its heating device 32 can be positioned closer to the sensor section formed by the solid electrolyte 12 with the electrodes 16 and 20, so that this results in an improved thermal coupling of the heating device 32. This permits a smaller load on the heating device 32 since, for the heating of the sensor section, intermediate layers no longer have to be heated as well.

Furthermore, due to the formation of the reference gas channel network by the electrode 20 itself, the effective electrode surface of the electrode 20 is enlarged vis-a-vis the reference gas, so that a pumping output of the electrode 20 is improved.

Finally, the contouring of the electrode 20 improves the overall stability of the electrochemical measuring sensor 10. The meander-shaped patterning of the electrode 20, which results from the embossing of the trench-shaped patterns 26, simultaneously forms stiffening ribs or stiffening regions which contribute to increasing the strength of the entire electrochemical measuring sensor 10. It is possible, in particular, to enlarge the electrode 20, in particular the electrode head 38, in relationship to the solid electrolyte surface, so that the margin regions of the solid electrolyte 12 remaining around the electrode 20 can be made smaller. Apart from the elimination of the above-cited intermediate layer for forming the air reference channels, a further miniaturization of the entire electrochemical measuring sensor 10 is hereby possible. Overall, the electrochemical measuring sensor 10 may thus be comprised of, for example, merely two films, with a first film being formed by the solid electrolyte 12 with the electrodes 16 and 20 and a second film by the cover plate 30 with the layer 34 comprising the heating conductors 36.

In the example that is illustrated, the trench-shaped patterns 26 are embossed so as to be essentially square, seen in cross section. Of course, any other cross sectional shape, for example, trapezoid, triangular, semicircular, etc. is suitable.

According to a further embodiment, the electrode 16 can, of course, also be embossed in an entirely analogous manner to enlarge the effective electrode surface. This enlarges the surface of the electrode 16 which is connected to the gas to be measured. Since, during the embossing process, the solid electrolyte 12 as well as the electrodes 16 and 20 are still present in their pasty form, that is in their green state, a contouring or patterning is possible in any conceivable manner. This means that, for example, by way of a corresponding contouring, the electrodes 16 or 20 can be "moved" to different horizontal planes of the electrochemical measuring sensor 10, so that, for the electrical contacting of the electrodes 16 or 20 line crossings can be implemented in a simple manner. Additionally, through-contacting can be facilitated because, in the embossed regions of the electrodes 16 or 20, the thickness of the solid electrolyte 12 between the corresponding electrode regions is reduced.

Figure 3:
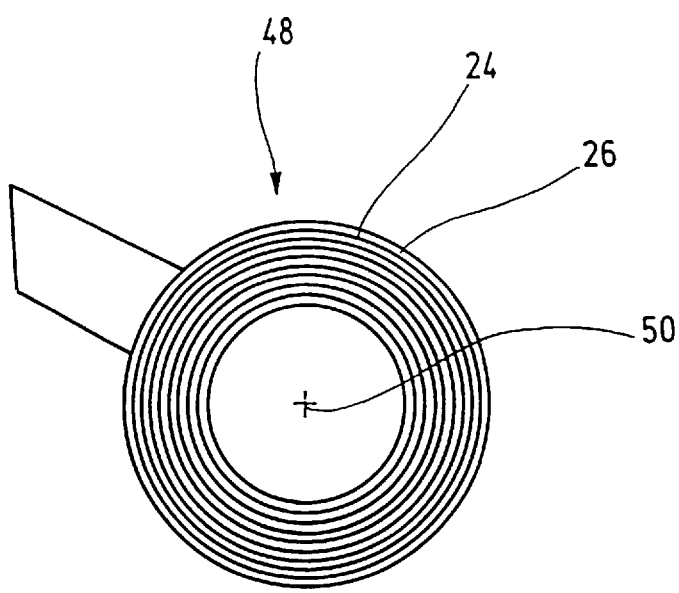
FIG. 3 a plan view onto an electrode exposed to a gas to be measured according to a further embodiment.

FIG. 3 shows an electrode 48 of an electrochemical measuring sensor in plan view. The electrode 48 shown here is used for electrochemical measuring sensors which are of a different design than the measuring sensor 10 illustrated in FIGS. 1 and 2. The electrodes essentially have the shape of a circular cylinder and are provided on their surface with circumferential contouring 24 extending coaxially with respect to a center point 50, which contours are formed by trench-shaped patterns 26 embossed into the electrode 48. If the electrode 48 illustrated in FIG. 3 having the surface shown there is exposed to a gas to be measured or to a reference gas, the effective electrode surface, which comes into contact with the gas to be measured or the reference gas, is considerably larger than that of an electrode having an entirely planar surface. This results in the advantages which were already mentioned above. Compared to the known electrodes, the electrodes 16, 20 or 48 according to the invention have a much higher effective electrode surface and thus a higher electrode activity while the space requirement remains unchanged and additional material is not used.

We claim:

1. An electrochemical measuring sensor having a solid electrolyte, a first electrode exposed to a gas to be measured and a second electrode exposed to a reference gas, with the electrodes being arranged on the solid electrolyte, and wherein at least one of the electrodes has a contouring on its surface that is exposed to the gas, with the contouring forming at least one trench-shaped groove, and with the trench-shaped groove being embossed into the surface of the electrode such that the electrode is impressed into the adjacent solid electrolyte in the region of the trench-shaped groove.

2. An electrochemical measuring sensor according to claim 1, wherein the trench-shaped groove has openings at least on one end surface of the solid electrolyte, which openings are connected with the reference gas.

3. An electrochemical measuring sensor according to claim 1, wherein a plurality of the trench-shaped grooves are provided and form a network structure.

4. An electrochemical measuring sensor according to claim 1, wherein the electrode provided with the groove is embedded in the solid electrolyte so that the solid electrolyte and the electrode have a planar surface.

5. An electrochemical measuring sensor according to claim 1, wherein a plurality of the trench-shaped grooves are provided and covered by a cover plate so that a channel network is formed which has openings at one end surface of the solid electrolyte.

6. A method for producing an electrochemical measuring sensor having a solid electrolyte, a first electrode exposed to a gas to be measured and a second electrode exposed to a reference gas, comprising applying at least one of the electrodes essentially layer-shaped on the solid electrolyte in a non-sintered state, contouring the at least one of the electrodes on its surface that is exposed to a gas by embossing at least one trench-shaped groove into the electrode surface while the solid electrolyte and the at least one electrode are in a non-sintered state, and subsequently sintering the solid electrolyte and the at least one electrode.

7. A method according to claim 6, wherein a network of grooves that cross one another is embossed into the surface of the at least one electrode.

8. A method according to claim 6 wherein the embossing step includes impressing the trench-shaped groove into the surface of the electrode such that the electrode is impressed into the adjacent solid electrolyte in the region of the trench-shaped groove.

* * * * *